United States Patent
Chen et al.

(10) Patent No.: US 10,156,528 B2
(45) Date of Patent: Dec. 18, 2018

(54) MOVABLE DIVIDED INSPECTION SYSTEM AND METHOD

(71) Applicant: NUCTECH COMPANY LIMITED, Beijing (CN)

(72) Inventors: Zhiqiang Chen, Beijing (CN); Yuanjing Li, Beijing (CN); Shangmin Sun, Beijing (CN); Yu Hu, Beijing (CN); Yuan Ma, Beijing (CN); Qiangqiang Wang, Beijing (CN); Long Du, Beijing (CN); Wei Li, Beijing (CN)

(73) Assignee: NUCTECH COMPANY LIMITED, Beijing (CN)

(*) Notice: Subject to any disclaimer, the term of this patent is extended or adjusted under 35 U.S.C. 154(b) by 0 days.

(21) Appl. No.: 15/691,748

(22) Filed: Aug. 31, 2017

(65) Prior Publication Data

US 2018/0059036 A1    Mar. 1, 2018

(30) Foreign Application Priority Data

Aug. 31, 2016   (CN) .......................... 2016 1 0786651

(51) Int. Cl.
*G01F 23/00*   (2006.01)
*G01N 23/04*   (2018.01)
(Continued)

(52) U.S. Cl.
CPC ........... *G01N 23/04* (2013.01); *G01V 5/0066* (2013.01); *G05D 1/0094* (2013.01); *G05D 2201/0207* (2013.01)

(58) Field of Classification Search
CPC .... G01V 5/0016; G01V 5/0025; G01N 23/04; G01N 23/046; G01N 23/20; G01N 2223/419
See application file for complete search history.

(56) References Cited

U.S. PATENT DOCUMENTS 5,764,683 A * 6/1998 Swift ................. G01N 23/04
378/196
5,838,759 A * 11/1998 Armistead ............ B66C 19/007
378/57

(Continued)

FOREIGN PATENT DOCUMENTS

EP          3032288 A1    6/2016
WO    2006036076 A1    4/2006

OTHER PUBLICATIONS

European Search Report dated Feb. 6, 2018 in the corresponding European application (European application No. 17188243.4).

*Primary Examiner* — Kiho Kim
(74) *Attorney, Agent, or Firm* — Kilpatrick Townsend & Stockton LLP (57) ABSTRACT

This invention relates to a movable divided inspection system and method, wherein the scanning inspection system comprises a first radiation source, a first detection means, a first automated guided vehicle and a second automated guided vehicle. The first radiation source is mounted on the first automated guided vehicle. The first detection means is mounted on the second automated guided vehicle. The first automated guided vehicle and the second automated guided vehicle are able to drive the first radiation source and the first detection means to a preset scan inspection position, so as to form a scanning passage for passage of an article to be scanned between the first and second automated guided vehicle, such that scanning inspection of said article to be scanned is realized by relative movement of said article to be scanned with reference to said first automated guided vehicle and said second automated guided vehicle.

14 Claims, 2 Drawing Sheets

(51) Int. Cl.
*G05D 1/00* (2006.01)
*G01V 5/00* (2006.01)

(56) References Cited

U.S. PATENT DOCUMENTS

| | | | |
|---|---|---|---|
| 6,843,599 | B2 | 1/2005 | Le et al. |
| 7,166,844 | B1 * | 1/2007 | Gormley .............. G01V 5/0016 250/358.1 |
| 2004/0247075 | A1 | 12/2004 | Johnson et al. |
| 2008/0025825 | A1 | 1/2008 | Fujiwara |
| 2008/0292050 | A1 * | 11/2008 | Goodenough ......... G01V 5/005 378/57 |
| 2010/0263948 | A1 * | 10/2010 | Couture ................... B25J 5/005 180/8.2 |
| 2011/0186739 | A1 * | 8/2011 | Foland ................. G01V 5/0008 250/360.1 |
| 2012/0093287 | A1 | 4/2012 | Singh |
| 2012/0093288 | A1 | 4/2012 | Mastronardi et al. |
| 2014/0136414 | A1 * | 5/2014 | Abhyanker ............ G06Q 50/28 705/44 |
| 2014/0189851 | A1 * | 7/2014 | Domke ................... G06F 21/31 726/17 |

\* cited by examiner

MOVABLE DIVIDED INSPECTION SYSTEM AND METHOD

CROSS REFERENCE TO RELATED APPLICATION

The present application claims the priority to Chinese Patent Application No. 201610786651.7, titled "MOVABLE DIVIDED INSPECTION SYSTEM AND METHOD", filed on Aug. 31, 2016 with the State Intellectual Property Office of the PRC, which is incorporated herein by reference in its entirety.

FIELD OF THE INVENTION

The present invention relates to the technical field of scanning inspection, and in particular relates to a movable divided inspection system and method.

BACKGROUND OF THE INVENTION

The existing container inspection system is commonly in such categories as a fixed gantry category, a mobile gantry category and a vehicle mounted category. Among them, the container inspection system of a fixed gantry category, is in such an inspection manner that a gantry is fixed on a scanning passage, while an article to be inspected passes through a scanning passage to accomplish the scanning; a mobile gantry category and a vehicle mounted category are in such a scanning inspection manner that a radiation source and a detector move, while an article to be scanned is fixed. Specifically, for a container system of a vehicle mounted category, its inspection system uses a universal truck chassis for carriage, and utilizes movement of a chassis vehicle to achieve the mobility of the entire inspection system. However, a mobile gantry category uses a track for carriage, so that the entire inspection is driven by a drive means on the track.

In the above container inspection systems of a vehicle mounted category and a mobile gantry category, the vehicle mounted category may be limited by emission of the chassis vehicle, left rubber/right rudder as well as other relevant road regulations, while the mobile gantry category is correspondingly limited with a need for use at a fixed site.

For an intelligent and integrated port, there may be a substantial use of unmanned automated guided vehicle (Automated Guided Vehicle, referred to as AGV for short) system. A movable container inspection as a link of a port makes it necessary for centralized management and control, and makes it necessary for effectuating unattended operation on an inspection system, but regardless of a vehicle mounted category and a mobile gantry category, such two movement manners are both hard to adapt to the demands of current intelligent ports.

On the other hand, for partial intelligent ports, especially intelligent ports that have already been implemented and accomplished in planning, the movement of AGV tends to need to perform lane-changing and steering at any position, without a quite fixed path. At the same time, magnetic nails of an equipment that guides an AGV are throughout the entire AGV advancing site, it is rather difficult for secondary civil engineering on the basis of the container inspection system, and moreover, it is also hard to find a fixed area to achieve passage of all AGV equipment. Thus, the existing inspection system of a fixed gantry category cannot adapt to the demands of current intelligent ports as well.

It is necessary to explain that, the information in the portion of the background art of the present invention is merely intended to enhance the understanding of the overall background of the present invention, and should not be construed as admitting or hinting in any form that the information constitutes the prior art already commonly known by a person skilled in the art.

SUMMARY OF THE INVENTION

It is an object of the present invention to provide a movable divided inspection system and method, so as to more flexibly and conveniently perform inspection of an article to be scanned.

In order to realize the aforementioned object, the present invention provides a movable divided inspection system, comprising a first radiation source, a first detection means, a first automated guided vehicle and a second automated guided vehicle, the first radiation source is mounted on the first automated guided vehicle, the first detection means is mounted on the second automated guided vehicle, the first automated guided vehicle and the second automated guided vehicle are able to drive the first radiation source and the first detection means to a preset scan inspection position, so as to form a scanning passage for passage of an article to be scanned between the first automated guided vehicle and the second automated guided vehicle, such that scanning inspection of the article to be scanned is realized by relative movement of the article to be scanned with reference to the first automated guided vehicle and the second automated guided vehicle.

Further, the article to be scanned is loaded by a third automated guided vehicle for driving the article to be scanned to move relative to the first automated guided vehicle and the second automated guided vehicle.

Further, the first radiation source is located within an advancing passage of the first automated guided vehicle, and/or the first detection means is located within an advancing passage of the second automated guided vehicle.

Further, the first detection means comprises a first detector and a detector arm, the first detector being disposed on the detector arm, for receiving the radiation emitted by the first radiation source.

Further, the detector arm is a straight arm, and a plurality of the first detectors are arranged along a length direction of the detector arm.

Further, the movable divided inspection system further comprises a position adjustment means for adjusting relative position relationship of the first radiation source and the detector arm, so that the detector arm is located within a radiation range of the first radiation source.

Further, the position adjustment means includes a second detector disposed on the detector arm, the second detector is arranged along a direction perpendicular to the axis of the detector arm so as to adjust relative position relationship of the first radiation source and the detector arm by a radiation dose received by the second detector.

Further, the second detector is disposed at a top and/or bottom of the detector arm.

Further, the position adjustment means includes a laser plane meter provided on the first automated guided vehicle and a laser receiver provided on the second automated guided vehicle, for adjusting a position of the laser receiver relative to the first automated guided vehicle according to a laser plane emitted by the laser plane meter, such that a relative position relationship of the detector arm and the first radiation source is adjusted.

Further, the movable divided inspection system comprises an adjustment means for adjusting a position of the detector arm with respect to the second automated guided vehicle or an angle with respect to a horizontal plane, so that the detector arm is located within a radiation range of the first radiation source.

Further, the adjustment means includes a push rod and a drive mechanism, the push rod being connected to the detector arm, the drive mechanism being provided on the second automated guided vehicle for driving the push rod to adjust a position and angle of the detector arm.

Further, the first radiation source and the first detection means are power supplied by power supply units of the first automated guided vehicle and the second automated guided vehicle, or power supplied by a power supply device independent from the power supply units of the first automated guided vehicle and the second automated guided vehicle.

Further, the first radiation source is at least partially embedded within the first automated guided vehicle, and/or the first detection means is at least partially embedded within the second automated guided vehicle.

Further, the movable divided inspection system further comprises a fourth automated guided vehicle, a second radiation source and a second detection means; the second radiation source is mounted on the fourth automated guided vehicle, the second detection means is mounted on either of the first automated guided vehicle and the second automated guided vehicle; or, the second detection means is mounted on the fourth automated guided vehicle, the second radiation source is mounted on either of the first automated guided vehicle and the second automated guided vehicle.

Further, the movable divided inspection system further comprises a fourth automated guided vehicle and a second detection means mounted on the fourth automated guided vehicle, the first radiation source for emitting radiations towards the first detection means and the second detection means.

In order to realize the aforementioned object, the present invention further provides an inspection method based on the aforementioned movable divided inspection system, the method comprising: providing a first automated guided vehicle mounted with a first radiation source and a second automated guided vehicle mounted with a first detection means;

driving the first automated guided vehicle and the second automated guided vehicle to move the first radiation source and the first detection means to a preset scan inspection position, and forming a scanning passage for passage of an article to be scanned between the first automated guided vehicle and the second automated guided vehicle; and effectuating scanning inspection of the article to be scanned by means of relative movement of the article to be scanned with reference to the first automated guided vehicle and the second automated guided vehicle.

Further, the method also comprises:

providing a third automated guided vehicle loaded with the article to be scanned; and when scanning inspection is performed of the article to be scanned, the first automated guided vehicle and the second automated guided vehicle are stationary, and the third automated guided vehicle moves, or the first automated guided vehicle and the second automated guided vehicle are synchronized in motion, and the third automated guided vehicle is stationary.

Further, before scanning inspection is performed of the article to be scanned, it further comprises:

adjusting relative position relationship of the first radiation source and the first detection means, so that the first detection means is located within a radiation range of the first radiation source.

Further, the adjusting relative position relationship of the first radiation source and the first detection means comprises:

a coarse adjustment step: effectuating coarse adjustment of relative position relationship of the first radiation source and the first detection means by moving the first automated guided vehicle or the second automated guided vehicle; and a fine adjustment step: effectuating fine adjustment of relative position relationship of the first radiation source and the first detection means by adjusting an adjustment means on the first detection means.

Further, the first detection means comprises a first detector and a detector arm, the detector arm being provided with a second detector, the second detector is arranged along with a direction perpendicular to the axis of the detector arm; and the adjusting relative position relationship of the first radiation source and the first detection means comprises: adjusting relative position relationship of the first radiation source and the detector arm by a radiation dose received by the second detector.

Further, the first automated guided vehicle is provided with a laser plane meter, the second automated guided vehicle is provided with a laser receiver, the first detection means comprises a first detector and a detector arm;

the adjusting relative position relationship of the first radiation source and the first detection means comprises:

adjusting a position of the laser receiver relative to the first automated guided vehicle according to a laser plane emitted by the laser plane meter, so as to adjust relative position relationship of the detector arm and the first radiation source.

According to the aforementioned technical solution, the present invention drives movement of the first radiation source and the first detection means by the automated guided vehicle, by mounting both the first radiation source and the first detection means on the automated guided vehicle, so that the first radiation source and the first detection means are also relatively flexible in movement, and not necessarily limited by a site, since the automated guided vehicle is relatively flexible in movement; moreover, the first radiation source and the first detection means are respectively mounted on different automated guided vehicles, i.e. the scanning inspection system which is of a divided structure presents better flexibility and adaptability; for intelligent ports that have already been implemented and accomplished in planning, it is possible to utilize a track available on the site so that there is no need for secondary civil engineering, and there is also no need for occupying a fixed area; compared to an inspection system of a vehicle mounted category, there is also not present with a limit in aspects such as emission of the chassis vehicle as well as relevant road regulations.

BRIEF DESCRIPTION OF THE ACCOMPANYING DRAWINGS

The drawings described herein are used to provide a further understanding of the present invention and constitute a part of the present application. The illustrative embodiments of the present invention as well as the descriptions thereof, which are used for explaining the present invention, do not constitute improper definitions on the present invention. In the drawings.

In the drawings: 1—first automated guided vehicle, 2—second automated guided vehicle, 3—third automated guided vehicle, 4—first radiation source, 5—detector arm, 6—container, 7—first detector.

DETAILED DESCRIPTION OF THE PREFERRED EMBODIMENTS

Next, the technical solution in the embodiments will be explicitly and completely described in combination with the drawings in the embodiments of the present invention. Apparently, the described embodiments are merely part of the embodiments of the present invention, rather than all the embodiments. On the basis of the embodiments of the present invention, all the other embodiments acquired by a person skilled in the art on the premise that no inventive effort is involved fall into the protection scope of the present invention.

In the description of the present invention, it is necessary to understand that, the azimuth or positional relations indicated by the terms "center", "transverse", "longitudinal", "front", "rear", "left", "right", "up", "down", "vertical", "horizontal", "top", "bottom", "within", "outside", which are based on the azimuth or positional relations illustrated by the drawings, are only for facilitating description of the present invention and simplifying the description, rather than indicating or implying that the device or element referred to has to present a particular azimuth, and be constructed and operated in a particular azimuth, so that it cannot be understood as limiting the protection scope of the present invention.

In view that the existing inspection systems of a fixed gantry category, a mobile gantry category and a vehicle mounted category all have the drawback that it is hard to adapt to the demands of current intelligent ports, after long-term practice and research, the inventor finds that, centralized management and control of the inspection scanning system may be realized by combining the AGV technology and the inspection scanning system and utilizing control of AGV, so as to better adapt to various different demands of current intelligent ports as well as other operational conditions.

Figure 1:
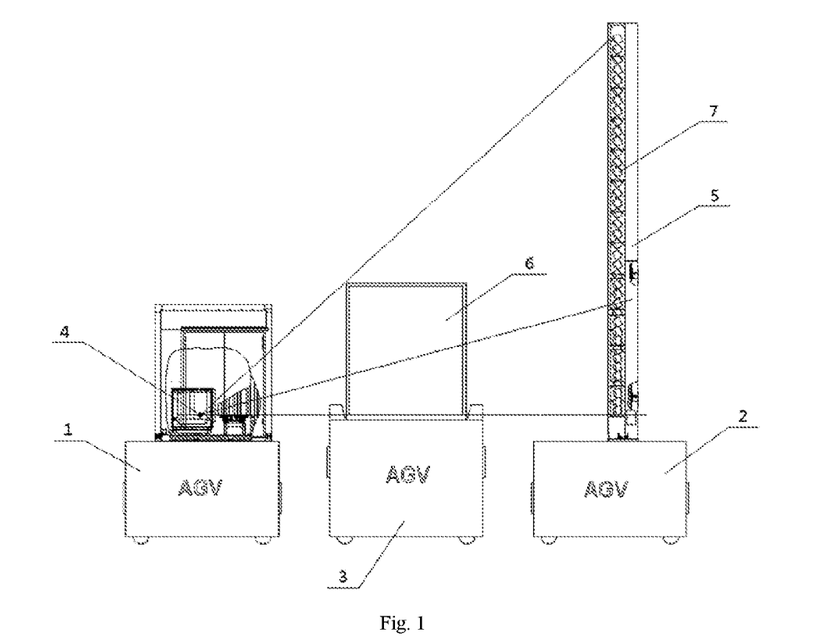
FIG. 1 is a schematic view of the structure of an embodiment of the movable divided inspection system according to the present invention.

On the basis of the aforementioned concept, the present invention sets forth a movable divided inspection system. As shown in FIG. 1, it is a schematic view of the structure of an embodiment of the movable divided inspection system according to the present invention. The scanning inspection system comprises a first radiation source 4, a first detection means having a detector, a first automated guided vehicle 1 and a second automated guided vehicle 2 (wherein, the automated guided vehicle is namely AGV), the first radiation source 4 is capable of emitting radiation for scanning an article to be scanned, the first detection means is capable of receiving the radiation emitted by the first radiation source 4 to effectuate scanning and inspection of the article to be scanned, the first radiation source 4 is mounted on the first automated guided vehicle 1, the first detection means is mounted on the second automated guided vehicle 2, i.e. the scanning inspection system which is of a divided structure presents favorable flexibility and adaptability.

The first automated guided vehicle 1 and the second automated guided vehicle 2 are dispatchable to drive the first radiation source 4 and the first detection means to a preset scan inspection position, and the first automated guided vehicle 1 and the second automated guided vehicle 2 therebetween form a scanning passage for passage of an article to be scanned; scanning inspection of the article to be scanned is realized by relative movement between the article to be scanned and the first automated guided vehicle 1 and the second automated guided vehicle 2.

In the aforementioned embodiment, movement of the first radiation source 4 and the first detection means is driven by the automated guided vehicle, by mounting both the first radiation source 4 and the first detection means on the automated guided vehicle, so that the first radiation source and the detection means are also relatively flexible in movement, and not necessarily limited by a site, since the automated guided vehicle is relatively flexible in movement; for intelligent ports that have already been implemented and accomplished in planning, it is possible to utilize a track available on the site so that there is no need for secondary civil engineering, and there is also no need for occupying a fixed area; compared to an inspection system of a vehicle mounted category, there is also not present with a limit in aspects such as emission of the chassis vehicle as well as relevant road regulations, so that it may adapt to different demands of more operational conditions.

As a preference of the aforementioned embodiment, the first radiation source 4 is at least partially embedded within the first automated guided vehicle 1 and/or the first detection means is at least partially embedded within the second automated guided vehicle 2. The first radiation source 4 and the first detection means are respectively mounted within the first automated guided vehicle 1 and the second automated guided vehicle 2 in an embedded manner, so that part of the first radiation source 4 and part of the first detection means are respectively mounted inside the first automated guided vehicle 1 and the second automated guided vehicle 2, which not only makes it possible that the first radiation source 4 and the first detection means are relatively stable and reliable in installation, but also makes it possible to reduce a height of the lowest radiation of the first radiation source 4, so that the top of the first automated guided vehicle 1 is closer to the bottom edge of the first radiation source 4, thus facilitating effectuating full scan of an article to be scanned.

It is necessary to explain that, when scanning is performed of the article to be scanned, the bottom edge of the first radiation source 4 should be on the same horizontal line as the bottom edge of the article to be scanned, and at the same time, the first detection means should be able to receive all the radiations emitted by the first radiation source 4 so as to form a complete scanning image.

On the basis of the aforementioned embodiment, in the movable divided inspection system, the article to be scanned is loaded by a third automated guided vehicle 3, which is capable of driving the article to be scanned to move relative to the first automated guided vehicle 1 and the second automated guided vehicle 2. That is to say, besides the movement of the first radiation source 4 and the first detection means by the automated guided vehicle, the movement of the article to be scanned may also be performed by the automated guided vehicle for movement, so as to facilitate centralized management and control of the first radiation source 4, the first detection means and the article to be scanned by the system.

When it is necessary to perform scanning inspection of the article to be scanned, it may be made that the first automated guided vehicle 1 and the second automated guided vehicle 2 are stationary, the third automated guided vehicle 3 passes through a scanning passage formed between the first automated guided vehicle 1 and the second automated guided vehicle 2, i.e. the first radiation source 4 and the first detection means are stationary, and the article to be scanned moves; it may also be made that the third automated guided vehicle 3 is stationary, while the first automated guided vehicle 1 and the second automated guided vehicle 2 move, and a scanning passage formed between the first automated guided vehicle 1 and the second automated guided vehicle 2 passes through the third automated guided vehicle 3, i.e. the article to be scanned is stationary, and the first radiation source 4 and the first detection means move.

Among them, the technical solution that the first radiation source 4 and the first detection means are stationary while the article to be scanned moves may better ensure constant relative position relationship of the first radiation source 4 and the first detection means, and make the scan more stable.

As a further improvement to the embodiment of the movable divided inspection system of the present invention, the first radiation source 4 is located within a range of a boundary line of the first automated guided vehicle 1 and/or the first detection means is located within a range of a boundary line of the second automated guided vehicle, such as to prevent collision or scratch taking place between the first automated guided vehicle 1 and/or the second automated guided vehicle 2 and other AGV devices, to prevent occurrence of safety accidents, and to avoid paralysis of the scanning inspection system.

As an embodiment of the first detection means in the movable divided inspection system of the present invention, the first detection means comprises a first detector 7 and a detector arm 5, the first detector 7 is disposed on the detector arm 5, and the first detector 7 is provided towards the first radiation source, so as to facilitate the first detector 7 in comprehensively receiving the radiation emitted by the first radiation source 4, and avoid incomplete image or affected image quality of the article to be scanned that has been acquired. The first detector 7 comprises a plurality of first detectors 7 which are uniformly distributed on the detector arm 5, so as to effectuate full inspection of the article to be scanned.

The specific structure and shape of the detector arm 5 may be flexibly provided, for example the detector arm 5 may be a non-straight arm, i.e. the detector arm 5 may be a bent arm or a folded arm consisting of a plurality of straight arms, as long as the detector arm 5 is capable of effectuating full scanning and inspection of the article to be scanned by providing the first detector 7. Certainly, in order to allow the second automated guided vehicle to avoid collision and scratch with other carriers, the shape of the detector arm 7 should be in a way such that it is within a range of a boundary line of the second automated guided vehicle 2.

In a preferred embodiment, the detector arm 5 is a straight arm, a plurality of first detectors 7 are arranged along a length direction of the detector arm 5, and the detector arm 5 is preferably arranged vertically, so that the detector arm 5 does not go beyond a range of a boundary line of the second automated guided vehicle 2. The detector arm 5 in the form of a straight arm is easy to manufacture, and the arrangement of the first detector 7 is also very easy, and is also capable of better avoiding collision and scratch.

Since the movable divided inspection system of the present invention is a divided structure, the first radiation source 4 and the first detection means are respectively provided on two automated guided vehicles, it is necessary to consider the problem of a match between the first radiation source 4 and the first detection means, i.e. it is necessary to ensure the cooperation between the first radiation source 4 and the first detection means by adjusting the relative position relationship between the first radiation source 4 and the detector arm 5. In other words, it is imperative to allow that the first detection means is capable of receiving all the radiations emitted by the first radiation source 4, to allow that the scanning image of the automated guided vehicle that has been acquired reaches maximum completeness and optimum quality.

The adjustments of the relative position relationship of the first radiation source 4 and the detector arm 5 include at least the adjustments of the relative position relationship in three directions including left-and-right, front-and-rear, and up-and-down as shown in the illustrated directions of FIG. 1.

In the left-and-right direction, the relative position relationship of the first radiation source 4 and the detector arm 5 may be determined by a width of the scanning passage formed by the first automated guided vehicle 1 and the second automated guided vehicle 2. Generally, the width of the scanning passage should be greater than that of the third automated guided vehicle 3 which carries the article to be scanned.

In the up-and-down direction, in order to ensure that the first detection means is able to comprehensively receive the radiation emitted by the first radiation source 4, a plurality of first detectors 7 may be provided on the detector arm 5 from the bottom to the top, and several first detectors 7 are additionally arranged beyond a theoretically maximum radiation range of the first radiation source 4, so as to ensure that the bottom and top of the detector arm 5 are both arranged with sufficient first detectors, and avoid missing the reception of the radiation, and to further cause loss of the scanning image.

In the front-and-rear direction, the adjustments of the relative position relationship of the first radiation source 4 and the detector arm 5, which are very complicated, will be introduced in detail below.

In an illustrative embodiment of the movable divided inspection system of the present invention, the scanning inspection system further comprises a position adjustment means for adjusting the relative position relationship of the first radiation source 4 and the detector arm 5 (here mainly refer to the relative position relationship in the front-and-rear direction in the illustrated directions of FIG. 1), to allow that the detector arm 5 is located within the radiation source face emitted by the first radiation source 4, so that the first detector 7 on the detector arm 5 is able to receive all the radiation emitted by the first radiation source 4, and to further make the scanning image of the article to be scanned that has been obtained reach optimum quality.

By means of the position adjustment means, the position of the first radiation source 4 may be adjusted, and the position of the detector arm 5 may also be adjusted as long as the relative positions therebetween satisfy the requirements.

The position adjustment means may have a plurality of specific structural forms, in which two specific embodiments are provided here.

In the first embodiment, the position adjustment means includes a second detector disposed on the detector arm, a direction in which the second detector is arranged and the axis of the detector arm 5 being perpendicular to each other, so as to adjust relative position relationship of the first radiation source 4 and the detector arm 5 by a radiation dose received by the second detector. The second detector comprises one or more, each the second detector is provided with a plurality of detecting pens, preferably, the setting direction of the plurality of detecting pens is perpendicular to the axis of the detector arm 5.

As the direction in which the second detector is arranged and the detector 5 may be perpendicular to each other, for example when it is necessary to adjust the relative position relationship of the first radiation source 4 and the detector arm 5 in the front-and-rear direction, the second detector may be arranged along the front-and-rear direction, so that according to a radiation dose received by each probe, it is possible to judge a direction in which the detector arm 5 deviates from the radiation source face emitted by the first radiation source 4, and after the deviation direction is determined, the adjustment of the relative position relationship of the detector arm 5 and the first radiation source 4 may be realized by moving the first automated guided vehicle 1 or the second automated guided vehicle 2.

Specifically, the probe with a maximum received radiation dose should be within the same plane as the first radiation source 4 and the detector arm 5. Preferably, the plane in which the probe with a maximum received radiation dose, the first radiation source 4 and the detector arm 5 are situated, and the movement trajectory of the article to be scanned are perpendicular to each other.

Preferably, the second detector is disposed at the top and/or bottom of the detector arm 5 so as to adjust the relative position relationship of the first radiation source 4 and the detector arm 5 according to a radiation dose received by the second detector disposed at the top and/or bottom, and it is also possible to ensure that the second detector is able to receive the radiation within all the radiation range of the first radiation source whilst adjusting the position.

In the second embodiment, the position adjustment means includes a laser plane meter provided on the first automated guided vehicle and a laser receiver provided on the second automated guided vehicle 2, to adjust a position of the laser receiver relative to the first automated guided vehicle 1 according to a laser plane emitted by the laser plane meter, so as to adjust relative position relationship of the detector arm 5 and the first radiation source 4.

In the embodiment, since the position of the laser plane meter relative to the first radiation source 4 may be acquired in advance, the position of the laser receiver relative to the detector arm 5 may also be acquired in advance, so that the relative position relationship of the detector arm 5 and the first radiation source 4 may be determined after the relative position relationship of the laser receiver and the laser plane meter are determined.

In the embodiment, it may be made that the laser plane meter is provided on the second automated guided vehicle 2, while the laser receiver is provided on the first automated guided vehicle 1.

Preferably, the laser receiver is disposed at a top and/or bottom of the detector arm 5.

In the aforementioned embodiment of adjusting the relative position relationship of the detector arm 5 and the first radiation source 4, besides the realization by adjusting the position of the first automated guided vehicle 1 or the second automated guided vehicle 2, it is also possible to realize the same by directly adjusting the position of the detector arm 5 itself. In a preferred embodiment, the detector arm 5 is provided with adjustment means for adjusting a position of the detector arm 5 with respect to the second automated guided vehicle 2 or an angle with respect to a horizontal plane (i.e. a tilt angle between the detector arm 5 and the horizontal plane), so that the detector arm 5 is located within a radiation source face emitted by the first radiation source 4.

As a preferred embodiment of the adjustment means, the adjustment means includes a push rod and a drive mechanism, the push rod being connected to the detector arm 5, the drive mechanism being provided on the second automated guided vehicle 2 and for driving the push rod to adjust a transverse position of the detector arm 5. The lateral position here refers to the relative position in the front-and-rear direction in the illustrated directions of FIG. 1. The drive mechanism may be a fuel tank, an air cylinder or a motor.

Preferably, the push rod and the drive mechanism each comprise two, respectively connected to the top and bottom of the detector arm 5, and the two push rods and drive mechanisms may be connected within the C-type frame to ensure the structural stability. Since the push rod is a long rod of a straight arm type, in the process of pushing movement of the detector arm 5 by the push rod, it may be favorable for the stability of the detector arm 5, and prevent the inclination of the detector arm 5.

When the two push rods are located at the same side of the detector arm 5, the position of the detector arm 5 relative to the second automated guided vehicle may be adjusted by simultaneously stretching or simultaneously retracting the push rods; the angle of the detector arm 5 relative to the horizontal plane may be adjusted by stretching one push rod thereof, whilst retracting the other push rod.

When the two push rods are located at an opposite side of the detector arm 5, the position of the detector arm 5 relative to the second automated guided vehicle may be adjusted, and the angle of the detector arm 5 relative to the horizontal plane may be also adjusted by stretching one push rod thereof, whilst retracting the other push rod. When the stretching amount of one push rod thereof is the same as the retracting amount of the other push rod, the position of the detector arm 5 relative to the second automated guided vehicle may be adjusted; when the stretching amount of one push rod thereof is different from the retracting amount of the other push rod, the angle of the detector arm 5 relative to the horizontal plane may be adjusted.

Certainly, the adjustment means further has many specific structures, which will no longer be repeated here, as long as their function can be realized.

In the aforementioned various embodiments, the first radiation source 4 and the first detection means may be respectively power supplied by power supply units of the first automated guided vehicle 1 and the second automated guided vehicle 2, and may also be power supplied by a power supply device independent from the power supply units of the first automated guided vehicle 1 and the second automated guided vehicle 2. Among them, the power supply units of the first automated guided vehicle 1 and the second automated guided vehicle 2 may be a lithium battery, and may also be a generator within the automated guided vehicle 1 and the second automated guided vehicle 2.

In one embodiment of the movable divided inspection system of the present invention, it further comprises a fourth automated guided vehicle, a second radiation source and a second detection means, in which the second radiation source is mounted on the fourth automated guided vehicle, the second detection means is mounted on either of the first automated guided vehicle 1 and the second automated guided vehicle 2; or, the second detection means is mounted on the fourth automated guided vehicle, the second radiation source is mounted on either of the first automated guided vehicle 1 and the second automated guided vehicle 2. That is, when the movable divided inspection system comprises a combination of multiple groups of radiation sources and detection means, an automated guided vehicle may be shared, to lessen a total amount of the automated guided vehicle, and reduce the overall cost.

In another embodiment of the movable divided inspection system of the present invention, it further comprises a fourth automated guided vehicle and a second detection means mounted on the fourth automated guided vehicle, the first radiation source 4 being capable of emitting radiations respectively towards a direction in which the first detection means is situated and a direction in which the second detection means is situated. That is, a radiation source capable of emitting radiation towards two directions is used to replace two independent radiation sources, so as to effectuate sharing a radiation source, and simplify the structure.

Besides, a rotation means may also be provided, and the first radiation source 4 is mounted on the rotation means, so that a second automated guided vehicle 2 is provided respectively at both sides of the first automated guided vehicle 1 which carries the first radiation source 4. The first radiation source 4 may rotate to a direction in which the radiation source is emitted by the first detection means on one second automated guided vehicle 2 therein, and may also rotate to a direction in which the radiation source is emitted by the first detection means on the other second automated guided vehicle 2, so as to effectuate sharing the first radiation source 4 and the first automated guided vehicle 1.

Certainly, when the radiation source and the detection means comprise three or more, a similar method may also be used to share an automated guided vehicle, a radiation source or a detection means, and the specific sharing method is no longer repeated here.

Figure 2:
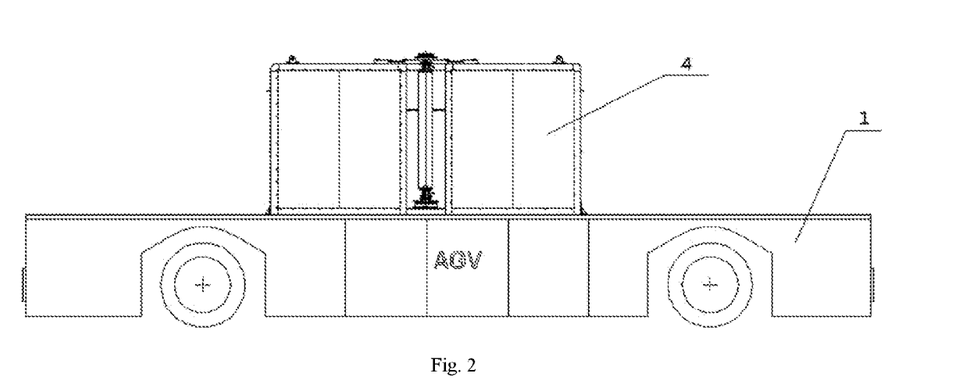
FIG. 2 is a schematic view of the structure of the first automated guided vehicle in an embodiment of the movable divided inspection system according to the present invention.

As shown in FIG. 2, it is a schematic view of the structure of the first automated guided vehicle mounted with the first radiation source 4. As can be seen from FIG. 3, the three automated guided vehicles used in the embodiments of the movable divided inspection system of the present invention have the same specification and dimension. In other words, the automated guided vehicle used in the scanning inspection system may use an automated guided vehicle available in intelligent ports, and there is no need to perform special transformation, so as to reduce the investment cost.

The movable divided inspection system of the present invention may be applied to various applicable occasions requiring article loading and article inspection, in which the article to be scanned may be various small or large articles, such as boxes and tanks. In one embodiment, the article to be scanned is a container, and the mobile divided inspection system is used for scanning and inspecting the container. The system, which is applied to intelligent ports, utilizes the control system of the ports to effectuate dispatching the container, the radiation source and the detection means by controlling the automated guided vehicle, so that the movable divided inspection system is able to realize centralized management and control, and improve the efficiency and reliability in operation of the ports.

Specifically, the navigation control system of the ports or docks may be utilized to monitor and control the scanning inspection system in real time, to effectuate automatic scan and inspection of the container, so as to provide a basis for follow-up inspection examination. When the customs needs to inspect a container, the navigation control system of a dock may designate an automated guided vehicle to convey the container to the scanning inspection system, and automatically accomplish the inspection process. In this way, it is possible to satisfy the demands of inspection examination within an intelligent unmanned port, and improve the market competitiveness of the vehicle scanning inspection system.

Further, considering that it is possible that a plurality of automated guided vehicles are present in an automated guided vehicle advancing site, in order to the mobile vehicle-mounted article inspection system to avoid scratching or colliding with other automated guided vehicles, it is preferable that the overall occupancy width of the movable divided inspection system of the present invention is no greater than a width of an advancing passage of two automated guided vehicles, such as to be able to effectuate passage of the third automated guided vehicle, without causing an influence over normal operation of other automated guided vehicle advancing passages during the advancement and during the scan.

In order to realize the object of the present invention, the present invention further sets forth an inspection method based on the movable divided inspection system in the aforementioned various embodiments, the method comprising:

providing a first automated guided vehicle 1 mounted with a first radiation source 4 and a second automated guided vehicle 2 mounted with a first detection means;

moving the first radiation source 4 and the first detection means to a preset scan inspection position, and forming a scanning passage for passage of an article to be scanned between the first automated guided vehicle 1 and the second automated guided vehicle 2, by dispatching the first automated guided vehicle 1 and the second automated guided vehicle 2;

effectuating scanning inspection of the article to be scanned by means of relative movement between the article to be scanned and the first automated guided vehicle 1 and the second automated guided vehicle 2.

Further, the method also comprises:
providing a third automated guided vehicle 3 loaded with the article to be scanned;
when scanning inspection is performed of the article to be scanned, the first automated guided vehicle 1 and the second automated guided vehicle 2 are stationary, and the third automated guided vehicle 3 moves; or
the first automated guided vehicle 1 and the second automated guided vehicle 2 are synchronized in motion, and the third automated guided vehicle 3 is stationary.

Before scanning inspection is performed of the article to be scanned, the method further comprises:
adjusting relative position relationship of the first radiation source 4 and the first detection means so that the first detection means is located within a radiation source face emitted by the first radiation source 4.

For such operation as to adjust relative position relationship of the first radiation source 4 and the first detection means, it comprises the following specific operational steps:
a coarse adjustment step: effectuating coarse adjustment of relative position relationship of the first radiation source 4 and the first detection means by moving the first automated guided vehicle 1 or the second automated guided vehicle 2; and
a fine adjustment step: effectuating fine adjustment of relative position relationship of the first radiation source 4 and the first detection means by adjusting an adjustment means on the first detection means.

In one embodiment, the first detection means comprises a first detector 7 and a detector arm 5, the detector arm 5 being provided with a second detector, a direction in which the second detector is arranged and the detector arm 5 being perpendicular to each other.

the adjusting relative position relationship of the first radiation source 4 and the first detection means comprises the following specific operations:

adjusting relative position relationship of the first radiation source 4 and the detector arm 5 by a radiation dose received by the second detector.

In another embodiment, the first automated guided vehicle 1 is provided with a laser plane meter, the second automated guided vehicle 2 is provided with a laser receiver, the first detection means comprises a first detector 7 and a detector arm 5, the adjusting relative position relationship of the first radiation source 4 and the first detection means comprises the following specific operations:

adjusting a position of the laser receiver relative to the first automated guided vehicle 1 according to a laser plane emitted by the laser plane meter, so as to adjust relative position relationship of the detector arm 5 and the first radiation source 4.

The technical effect realized by the inspection method of the present invention may refer to the aforementioned relevant description of the scanning inspection system, and will no longer be repeated here.

Next, the specific structure and operational process of one embodiment of the movable divided inspection system and method of the present invention will be explained in combination with FIGS. 1-3.

As shown in FIGS. 1 and 2, the first radiation source 4 is embedded into the first automated guided vehicle 1, the detector arm 5 is embedded into the second automated guided vehicle 2, the container 6 is carried by the third automated guided vehicle 3 and a plurality of first detectors 7 are provided on the detector arm 5.

During the transport and operation, the first radiation source 4, the detector arm 5, and the container 6 are all within a limit range of respective automated guided vehicles, so as to avoid collision and scratching with other AGV small vehicles.

Before the scanning and inspection of the container 6, a second detector perpendicular to the first detector 7 is first placed at the top and bottom of the detector arm 5, for checking a position at which the radiation dose is maximum. According to a position at which the first detector 7 is deviated, the position and angle of the detector arm are adjusted by moving the first automated guided vehicle 1 and the second automated guided vehicle 2 or the push rod provided at the top of the detector arm 5, to allow that the first detection means is located within a radiation source face emitted by the first radiation source 4, so as to reach an optimum quality of the scanning image regarding the container that has been obtained.

In addition, a laser plane meter may also be mounted on the second automated guided vehicle 1 on which the first radiation source 4 is mounted, and a laser receiver (or a point finder) for detecting laser is mounted on the top and bottom of the detector arm 5. The position of the detector arm 5 is adjusted according to a laser plane so that the first detection means is located within a radiation source face emitted by the first radiation source 4.

Figure 3:
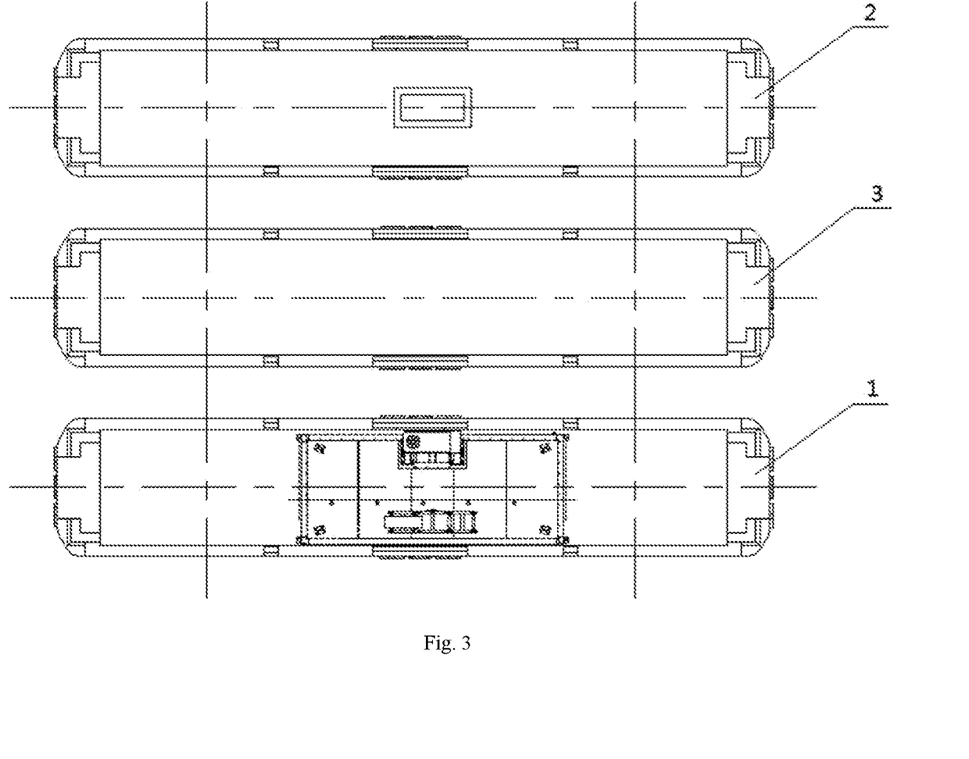
FIG. 3 is a top view of the embodiment of FIG. 1.

As shown in FIG. 3, when it is necessary to scan and inspect the container 6, the third automated guided vehicle 3 carrying the inspected container 6 travels in a uniform velocity from a scanning passage between the first automated guided vehicle 1 and the second automated guided vehicle 2, to complete the scanning inspection of the container 6.

With reference to a plurality of embodiments of the movable divided inspection system and method of the present invention, it can be seen that the embodiments of the movable divided inspection system of the present invention disclose a movable divided inspection system based on the automated guided vehicle technology, which scanning inspection system may automatically adjust relative position relationship of the radiation source and the detection means so that the detection means is located within the radiation source face emitted by the radiation source to obtain a relatively complete scanning image with a good quality. Further, the radiation source and the detection means, which are both located within a limit range of the automated guided vehicle, may avoid collision with the automated guided vehicle. By means of the flexibility in motion and the reliability in control of the automated guided vehicle, the scanning inspection system of the present invention may adapt to different demands of multiple operational conditions.

Finally, it should be explained that: the aforementioned embodiments are only used to describe the technical solution of the present invention rather than limiting the same; although detailed explanations are made to the present invention by referring to preferred embodiments, a common technical person in the art should understand that: it is still possible to make amendments to the embodiments of the present invention or make equivalent replacements to part of the technical features; without departing from the spirit and scope of the present invention, they should all be covered in the scope of the technical solution for which protection is sought in the present invention.

The invention claimed is:

1. A movable divided inspection system, comprising:
a first radiation source, a first detection means, a first automated guided vehicle and a second automated guided vehicle, said first radiation source is mounted on said first automated guided vehicle, said first detection means is mounted on said second automated guided vehicle, said first automated guided vehicle and said second automated guided vehicle are able to drive said first radiation source and said first detection means to a preset scan inspection position, so as to form a scanning passage for passage of an article to be scanned between said first automated guided vehicle and said second automated guided vehicle, such that scanning inspection of said article to be scanned is realized by relative movement of said article to be scanned with reference to said first automated guided vehicle and said second automated guided vehicle, said first detection means comprises a first detector and a detector arm, said first detector being disposed on the detector arm, for receiving the radiation emitted by said first radiation source, the movable divided inspection system further comprising a position adjustment device for adjusting relative position relationship of said first radiation source and said detector arm, so that said detector arm is located within a radiation range of said first radiation source, said position adjustment device includes a second detector disposed on said detector arm, said second detector is arranged along a direction perpendicular to the axis of said detector arm to adjust relative position relationship of said first radiation source and said detector arm by a radiation dose received by said second detector.

2. The movable divided inspection system according to claim 1, wherein said article to be scanned is loaded by a third automated guided vehicle for driving said article to be scanned to move relative to said first automated guided vehicle and said second automated guided vehicle.

3. The movable divided inspection system according to claim 1, wherein said first radiation source is located within an advancing passage of said first automated guided vehicle, and/or said first detection means is located within an advancing passage of said second automated guided vehicle.

4. The movable divided inspection system according to claim 1, wherein said detector arm is a straight arm, and a plurality of said first detectors are arranged along a length direction of said detector arm.

5. The movable divided inspection system according to claim 1, wherein said second detector is disposed at a top and/or bottom of said detector arm.

6. The movable divided inspection system according to claim 1, wherein said position adjustment device includes a laser plane meter provided on said first automated guided vehicle and a laser receiver provided on said second automated guided vehicle, for adjusting a position of said laser receiver relative to said first automated guided vehicle according to a laser plane emitted by said laser plane meter, such that a relative position relationship of said detector arm and said first radiation source is adjusted.

7. The movable divided inspection system according to claim 1, further comprising an adjustment device for adjusting a position of said detector arm with respect to said second automated guided vehicle or an angle with respect to a horizontal plane, so that said detector arm is located within a radiation range of said first radiation source.

8. The movable divided inspection system according to claim 7, wherein said adjustment device includes a push rod and a drive mechanism, said push rod being connected to said detector arm, said drive mechanism being provided on said second automated guided vehicle for driving said push rod to adjust a position and angle of said detector arm.

9. The movable divided inspection system according to claim 1, wherein said first radiation source and said first detection means are power supplied by power supply units of said first automated guided vehicle and said second automated guided vehicle, or power supplied by a power supply device independent from the power supply units of said first automated guided vehicle and said second automated guided vehicle.

10. The movable divided inspection system according to claim 1, wherein said first radiation source is at least partially embedded within said first automated guided vehicle, and/or said first detection means is at least partially embedded within said second automated guided vehicle.

11. The movable divided inspection system according to claim 1, further comprising a fourth automated guided vehicle, a second radiation source and a second detection means; said second radiation source is mounted on said fourth automated guided vehicle, said second detection means is mounted on either of said first automated guided vehicle and said second automated guided vehicle; or, said second detection means is mounted on said fourth automated guided vehicle, said second radiation source is mounted on either of said first automated guided vehicle and said second automated guided vehicle.

12. The movable divided inspection system according to claim 1, further comprising a fourth automated guided vehicle and a second detection means mounted on said fourth automated guided vehicle, said first radiation source for emitting radiations towards said first detection means and said second detection means.

13. A movable divided inspection system, comprising:
a first radiation source, a first detection means, a first automated guided vehicle and a second automated guided vehicle, said first radiation source is mounted on said first automated guided vehicle, said first detection means is mounted on said second automated guided vehicle, said first automated guided vehicle and said second automated guided vehicle are able to drive said first radiation source and said first detection means to a preset scan inspection position, so as to form a scanning passage for passage of an article to be scanned between said first automated guided vehicle and said second automated guided vehicle, such that scanning inspection of said article to be scanned is realized by relative movement of said article to be scanned with reference to said first automated guided vehicle and said second automated guided vehicle, said first detection means comprises a first detector and a detector arm, said first detector being disposed on the detector arm, for receiving the radiation emitted by said first radiation source, the movable divided inspection system further comprising a position adjustment device for adjusting relative position relationship of said first radiation source and said detector arm, so that said detector arm is located within a radiation range of said first radiation source, wherein said position adjustment device includes a laser plane meter provided on said first automated guided vehicle and a laser receiver provided on said second automated guided vehicle, for adjusting a position of said laser receiver relative to said first automated guided vehicle according to a laser plane emitted by said laser plane meter, such that a relative position relationship of said detector arm and said first radiation source is adjusted.

14. A movable divided inspection system, comprising:
a first radiation source, a first detection means, a first automated guided vehicle and a second automated guided vehicle, said first radiation source is mounted on said first automated guided vehicle, said first detection means is mounted on said second automated guided vehicle, said first automated guided vehicle and said second automated guided vehicle are able to drive said first radiation source and said first detection means to a preset scan inspection position, so as to form a scanning passage for passage of an article to be scanned between said first automated guided vehicle and said second automated guided vehicle, such that scanning inspection of said article to be scanned is realized by relative movement of said article to be scanned with reference to said first automated guided vehicle and said second automated guided vehicle, wherein said first detection means comprises a first detector and a detector arm, said first detector being disposed on the detector arm, for receiving the radiation emitted by said first radiation source, further comprising an adjustment device for adjusting a position of said detector arm with respect to said second automated guided vehicle or an angle with respect to a horizontal plane, so that said detector arm is located within a radiation range of said first radiation source, wherein said adjustment device includes a push rod and a drive mechanism, said push rod being connected to said detector arm, said drive mechanism being provided on said second automated guided vehicle for driving said push rod to adjust a position and angle of said detector arm.

* * * * *